United States Patent [19]
Miyagawa et al.

[11] Patent Number: 5,555,087
[45] Date of Patent: Sep. 10, 1996

[54] METHOD AND APPARATUS FOR EMPLOYING A LIGHT SOURCE AND HETERODYNE INTERFEROMETER FOR OBTAINING INFORMATION REPRESENTING THE MICROSTRUCTURE OF A MEDIUM AT VARIOUS DEPTHS THEREIN

[75] Inventors: Ichirou Miyagawa; Masahiro Toida, both of Kanagawa-ken, Japan

[73] Assignee: Fuji Photo Film Co., Ltd., Kanagawa, Japan

[21] Appl. No.: 260,223

[22] Filed: Jun. 14, 1994

[30] Foreign Application Priority Data

Jun. 15, 1993 [JP] Japan .................... 5-143362

[51] Int. Cl.⁶ ...................... G01B 9/02; G01B 11/02
[52] U.S. Cl. .............. 356/345; 356/349; 356/357
[58] Field of Search ........................... 356/345, 349, 356/357–358, 360

[56] References Cited

U.S. PATENT DOCUMENTS

| | | | |
|---|---|---|---|
| 4,627,731 | 12/1986 | Waters et al. | 356/345 |
| 4,892,406 | 1/1990 | Waters | 356/345 |
| 5,293,215 | 3/1994 | Pfendler et al. | 356/349 |
| 5,321,501 | 6/1994 | Swanson et al. | 356/345 |
| 5,343,290 | 8/1994 | Batchelder et al. | 356/349 |

FOREIGN PATENT DOCUMENTS 2582807  12/1986  France .................... 356/349

OTHER PUBLICATIONS

"Science", David Huang, et al., 1991, vol. 254, pp. 1178–1181.

Primary Examiner—Frank Gonazlez
Assistant Examiner—Jason D. Eisenberg
Attorney, Agent, or Firm—Sughrue, Mion, Zinn, Macpeak & Seas

[57] ABSTRACT

A low coherence light beam is split into first and second light beams, and the frequency of the first light beam is shifted. The first and second light beams are then combined with each other at a position at which the optical path difference between the two light beams is larger than the coherence length of the low coherence light beam. The combined light beam is guided to a position in the vicinity of a medium having light scattering properties and split into a third light beam, which travels reversely to the direction of travel of the combined light beam, and a fourth light beam, which is irradiated to the medium. A light beam scattered backwardly from a predetermined depth in the medium is caused to interfere with the third light beam, and the intensity of the resulting interference light beam is detected. Optical heterodyne detection of the intensity of the backward scattered light beam is carried out in accordance with the detected intensity of the interference light beam, and information representing the microstructure of the predetermined deed portion in the medium is thereby obtained.

7 Claims, 3 Drawing Sheets

METHOD AND APPARATUS FOR EMPLOYING A LIGHT SOURCE AND HETERODYNE INTERFEROMETER FOR OBTAINING INFORMATION REPRESENTING THE MICROSTRUCTURE OF A MEDIUM AT VARIOUS DEPTHS THEREIN

BACKGROUND OF THE INVENTION

1. Field of the Invention

This invention relates to a method and apparatus for obtaining tomographic information. This invention particularly relates to a method and apparatus for obtaining tomographic information, wherein a light beam scattered backwardly from a medium having light scattering properties is detected, and information representing the microstructure at the surface of the medium or at a portion deep from the surface of the medium is obtained from the backward scattered light beam.

2. Description of the Prior Art

Various methods and apparatuses for obtaining tomographic information have heretofore been proposed wherein tomographic information, such as a tomographic image, of a medium having light scattering properties, such as a living body, is obtained such that the medium may not be invaded.

As one of the methods for obtaining tomographic information, optical coherence tomography (hereinafter referred to as OCT) has heretofore been used. With the OCT, a low coherence light beam is split into a light beam, which is to be irradiated to a medium, and a reference light beam, and a Michelson type of interferometer is constituted by the two split light beams. Optical heterodyne detection is carried out on the interference light beam, which is obtained from the interferometer, and the intensity of a light beam scattered backwardly from the medium is thereby detected. From the detected intensity of the backward scattered light beam, the tomographic information at the surface of the medium or a deep portion in the medium is obtained. Tomographic information at an arbitrary deep potion in the medium can be obtained by modulating the optical path length of the reference light.

However, with the OCT, the coherence length of the low coherence light beam is short. Therefore, in cases where the medium, the tomographic information of which is to be obtained, is very large and must therefore be located at a position away from the position at which the low coherence light beam is split into the light beam to be irradiated to the medium and the reference light beam, it is necessary for the reference light beam to follow a long optical path from the position at which the two light beams are split from each other. Accordingly, the problems occur in that, in order for the variability of the optical path length to be kept large, the size of the apparatus for obtaining tomographic information cannot be kept small.

As a technique for solving the problems described above, a technique, wherein a reference light beam and a light beam to be irradiated to a medium are respectively guided through different single mode optical fiber bundles, has been proposed by David Huang, et al. in "Science," 1991, Vol. 254, pp. 1178–1181. With the proposed technique, a frequency shifting mechanism for shifting the frequency of the reference light beam is located in the optical path of the reference light beam, and a heterodyne signal is thereby obtained. Also, a mechanical mechanism for quickly displacing the leading end of the optical path of the light beam to be irradiated to the medium, i.e. the leading end of the single mode optical fiber bundle, along the optical axis direction is provided, and the information in the depth direction in the region inside of the medium is thereby obtained.

However, with the conventional technique described above, the leading end of the single mode optical fiber bundle must be displaced quickly by the mechanical mechanism. In addition, the single mode optical fiber bundle, through which the reference light beam passes, and the single mode optical fiber bundle, through which the light beam to be irradiated to the medium passes, are independent of each other. Therefore, the two single mode optical fiber bundles are liable to be affected in different manners by external vibrations or thermal disturbance. Accordingly, the frequency of a beat signal generated from the interference between the light beam, which has been irradiated to the medium and has thereafter been scattered backwardly from the medium, and the reference light beam, the frequency of which has been shifted, is affected in an unexpected manner by the external vibrations or thermal disturbance. In such cases, a signal, which has a low signal-to-noise ratio (S/N ratio), is obtained from the optical heterodyne detection.

Also, the conventional technique described above has the problems in that a long time is required for the two-dimensional scanning of the leading end of the single mode optical fiber bundle. In cases where image optical fiber bundles (ordinarily, multimode image optical fiber bundles) are employed in order to solve such problems, there is the risk that mode coupling occurs with each of the light beams, which are guided through the respective optical fiber bundles, due to external vibrations or thermal disturbance applied independently to the respective optical fiber bundles. A light beam resulting from superposition of the light beams, which have suffered from different mode coupling during the passage through the respective optical fiber bundles, one upon the other will have no significant effect.

SUMMARY OF THE INVENTION

The primary object of the present invention is to provide a method for obtaining tomographic information wherein, in cases where light beams are guided without an optical fiber bundle being utilized, an optical path of a light beam to be irradiated to a medium and an optical path of a reference light beam need not necessarily be provided independently of each other.

Another object of the present invention is to provide a method for obtaining tomographic information wherein, in cases where light beams are guided through an optical fiber bundle to a position in the vicinity of a medium and are caused to scan the surface of the medium in two directions, a mechanical mechanism for quickly displacing the leading end of the optical fiber bundle need not necessarily be provided.

A further object of the present invention is to provide a method for obtaining tomographic information wherein, even if external vibrations or thermal disturbance occur on an optical fiber bundle, or the like, tomographic information of a medium having light scattering properties is obtained with a high S/N ratio.

The specific object of the present invention is to provide an apparatus for carrying out the method for obtaining tomographic information.

With a method for obtaining tomographic information in accordance with the present invention, a low coherence light beam is split into a light beam, the frequency of which is shifted from its original frequency, and a light beam having the original frequency. The two split light beams are passed through optical paths, which have a certain value of optical path difference, specifically an optical path difference larger than the coherence length of the low coherence light beam, therebetween. The two split light beams are then combined with each other such that they may not interfere with each other. The combined light beam, which is thus obtained by combining the two split light beams, is caused to follow a single optical path and to travel to a position in the vicinity of a medium. Thereafter, part of the combined light beam, which has traveled to the position in the vicinity of the medium, is caused to travel reversely to the direction of travel of the combined light beam, and the remaining part of the combined light beam is irradiated to the medium. The light beam, the direction of travel of which has thus been reversed, contains the component of the light beam, the frequency of which has been shifted from its original frequency, and the component of the light beam having the original frequency, the components of the two light beams having the optical path difference described above. Also, as in the light beam, the direction of travel of which has been reversed, the light beam irradiated to the medium contains such components of the two light beams.

The light beam, which has thus been irradiated to the medium, is reflected or scattered from the surface of the medium or a portion of the medium deep from its surface. The backward scattered light beam, which has thus been reflected or scattered from the surface of the medium or a deep portion in the medium, travels in the same direction as the aforesaid light beam, the direction of travel of which has been reversed. The backward scattered light beam is then combined with the aforesaid light beam, the direction of travel of which has been reversed. The light beam, which has been irradiated to the medium and reflected or scattered by the medium, passes through the optical path, which is longer than the optical path of the aforesaid light beam, the direction of travel of which has been reversed. Therefore, when the backward scattered light beam is combined with the aforesaid light beam, the direction of travel of which has been reversed, the component of the light beam, which is one of the components of the two light beams having the aforesaid optical path difference therebetween and constituting the aforesaid reversed light beam, and which has passed through the optical path having the longer optical path length than the optical path length of the other component, is caused to interfere with the component of the light beam, which is one of the components of the two light beams having the aforesaid optical path difference therebetween and constituting the backward scattered light beam, and which has passed through the optical path having the shorter optical path length than the optical path length of the other component. The beat signal resulting from the interference is detected, and tomographic information of the medium is then obtained from the detected beat signal.

Specifically, the present invention provides a method for obtaining tomographic information, comprising the steps of:

i) splitting a low coherence light beam into a first light beam and a second light beam, which travel along two different optical paths, ii) shifting the frequency of the first light beam to a frequency, which is slightly different from the original frequency of the first light beam, iii) combining the first light beam, the frequency of which has been shifted, and the second light beam with each other at a position at which the optical path difference between the first light beam and the second light beam is larger than the coherence length of the low coherence light beam, iv) guiding the combined light beam, which has thus been obtained by combining the first light beam and the second light beam with each other, to a position in the vicinity of a medium, which has light scattering properties and tomographic information of which is to be obtained, v) splitting the combined light beam, which has thus been guided to the position in the vicinity of the medium having light scattering properties, into a third light beam, which travels reversely to the direction of travel of the combined light beam, and a fourth light beam, which continues to travel along the direction of travel of the combined light beam and is thus irradiated to the medium having light scattering properties, vi) combining a backward scattered light beam, which comes from the medium having light scattering properties when the fourth light beam is irradiated to the medium having light scattering properties, and the third light beam with each other, vii) detecting the intensity of an interference light beam obtained from interference of:

a) the light beam component, which is one of the components of the first light beam and the second light beam constituting the third light beam and which has passed through the optical path having the longer optical path length than the optical path length of the other component, the optical path length being taken from the position, at which the first light beam and the second light beam are split from each other, to the position, at which the first light beam and the second light beam are thereafter combined with each other, and b) the light beam component, which is one of the components of the first light beam and the second light beam constituting the backward scattered light beam and which has passed through the optical path having the shorter optical path length than the optical path length of the other component, the optical path length being taken from the position, at which the first light beam and the second light beam are split from each other, to the position, at which the first light beam and the second light beam are thereafter combined with each other, and viii) carrying out optical heterodyne detection of the intensity of the backward scattered light beam in accordance with the detected intensity of the interference light beam, whereby information representing the microstructure of a predetermined deep portion in the medium having light scattering properties is obtained.

The method for obtaining tomographic information in accordance with the present invention may be modified such that the optical path difference may be modulated arbitrarily. In such cases, the information representing the microstructure of an arbitrary deep portion in the medium having light scattering properties can be obtained.

By way of example, as the low coherence light beam, a light beam, which is produced by a super-luminescent diode (SLD) and has a coherence length falling within the range of 40 µm to 50 µm, or a light beam, which is produced by a light emitting diode (LED) has a coherence length falling within the range of 0 to 20 µm, may be employed. A light beam produced by an SLD has good directivity and should preferably be employed as the low coherence light beam.

The backward scattered light beam contains not only the light beam, which is scattered backwardly from a deep portion in the medium, but also the light beam, which is reflected from the surface of the medium. The position of the surface or the deep portion corresponds to the difference between the optical path length of the first light beam and the optical path length of the second light beam.

The term "backward scattered light beam" as used herein means the light beam, which is scattered by a microstructure, such as a light scattering substance, of the medium and is thus radiated out of the medium in the direction reverse to the direction of incidence of the light beam upon the medium.

The present invention also provides an apparatus for carrying out the method for obtaining tomographic information in accordance with the present invention. Specifically, the present invention also provides an apparatus for obtaining tomographic information, comprising:

i) a light source for producing a low coherence light beam, ii) an optical system for splitting the low coherence light beam, which has been produced by the light source, into a first light beam and a second light beam, which travel along two different optical paths, and combining the first light beam and the second light beam with each other at a position at which the optical path difference between the first light beam and the second light beam is larger than the coherence length of the low coherence light beam, iii) a frequency shifter for shifting the frequency of the first light beam to a frequency, which is slightly different from the original frequency of the first light beam, iv) a light guide means for guiding the combined light beam, which has thus been obtained by combining the first light beam and the second light beam with each other, to a position in the vicinity of a medium, which has light scattering properties and tomographic information of which is to be obtained, v) an optical member for splitting the combined light beam, which has thus been guided to the position in the vicinity of the medium having light scattering properties, into a third light beam, which travels reversely to the direction of travel of the combined light beam, and a fourth light beam, which continues to travel along the direction of travel of the combined light beam and is thus irradiated to the medium having light scattering properties, the optical member thereafter combining a backward scattered light beam, which comes from the medium having light scattering properties when the fourth light beam is irradiated to the medium having light scattering properties, and the third light beam with each other, vi) a photodetector for detecting the intensity of an interference light beam obtained from interference of:
  a) the light beam component, which is one of the components of the first light beam and the second light beam constituting the third light beam and which has passed through the optical path having the longer optical path length than the optical path length of the other component, the optical path length being taken from the position, at which the first light beam and the second light beam are split from each other, to the position, at which the first light beam and the second light beam are thereafter combined with each other, and
  b) the light beam component, which is one of the components of the first light beam and the second light beam constituting the backward scattered light beam and which has passed through the optical path having the shorter optical path length than the optical path length of the other component, the optical path length being taken from the position, at which the first light beam and the second light beam are split from each other, to the position, at which the first light beam and the second light beam are thereafter combined with each other, and vii) an optical heterodyne detection means for detecting the intensity of the backward scattered light beam in accordance with the intensity of the interference light beam, which has been detected by the photodetector, whereby information representing the microstructure of a predetermined deep portion in the medium having light scattering properties is obtained.

The apparatus for obtaining tomographic information in accordance with the present invention may be modified such that an optical path length modulating means may be located in either one of the optical path of the first light beam and the optical path of the second light beam. In such cases, the information representing the microstructure of an arbitrary deep portion in the medium having light scattering properties can be obtained by modulating the optical path length of the optical path, in which the optical path length modulating means is located.

As the optical member, a semi-transparent mirror may be employed. Also, as the light guide means, an optical fiber bundle may be employed. As the optical fiber bundle, a single mode optical fiber bundle or an image optical fiber bundle (multimode) may be used.

In cases where an image optical fiber bundle is employed or in cases where a plurality of single mode optical fiber bundles are bundled and utilized in the same manner as in the image optical fiber bundle, the tomographic information of the medium can be obtained in two directions and simultaneously. Also, in such cases, a two-dimensional image representing the tomographic information of the medium can be obtained. Further, the tomographic information of the medium can be obtained in two directions and simultaneously by employing a scanning means for scanning the light guide means and the optical member together or for scanning the optical fiber bundle in two directions in a plane, which is normal to the direction along which the light guide means or the optical fiber bundle extends.

With the method and apparatus for obtaining tomographic information in accordance with the present invention, the low coherence light beam is split into the two light beams, and the two split light beams are then combined with each other. Before the two split light beams are combined with each other, the frequency of either one of the two split light beams is shifted slightly. Therefore, if the optical path lengths of the two split light beams are approximately equal to each other, an interference light beam, the optical intensity of which repeatedly becomes high and low at a frequency equal to the difference between the frequencies of the two split light beams, will occur when the two split light beams are superposed one upon the other. However, with the method and apparatus for obtaining tomographic information in accordance with the present invention, the optical path difference between the two split light beams is set to be larger than the coherence length of the low coherence light beam. Therefore, when the two split light beams are superposed one upon the other, no interference light beam occurs. The superposed light beam (i.e., the combined light beam), which is obtained by superposing the two split light beams one upon the other, serves as the light beam composed of two light beams, which have slightly different frequencies and have passed through the optical paths having different optical path lengths.

The combined light beam travels along the predetermined optical path to the position in the vicinity of the medium. Thereafter, part of the combined light beam is caused to travel reversely to the direction of travel of the combined light beam. The remaining part of the combined light beam continues to travel along the direction of travel of the combined light beam and is thus irradiated to the medium.

When the remaining part of the combined light beam is irradiated to the medium, the backward scattered light beam occurs from the medium. The backward scattered light beam is then combined with the light beam, the direction of travel of which has been reversed. The optical path length of the light beam, which has been irradiated to the medium and is then combined as the backward scattered light beam with the light beam, the direction of travel of which has been reversed, is longer by the length of the optical path from the position, at which the two light beams were split from each other, to the position, at which the two light beams are combined with each other, than the optical path length of the light beam, the direction of travel of which has been reversed. Therefore, when the backward scattered light beam is combined with the aforesaid light beam, the direction of travel of which has been reversed, the component of the light beam, which is one of the components of the two light beams having the aforesaid optical path difference therebetween and constituting the aforesaid reversed light beam, and which has passed through the optical path having the longer optical path length than the optical path length of the other component, is caused to interfere with the component of the light beam, which is one of the components of the two light beams having the aforesaid optical path difference therebetween and constituting the backward scattered light beam, and which has passed through the optical path having the shorter optical path length than the optical path length of the other component. In this manner, the interference light beam occurs.

The backward scattered light beam is radiated from various positions with respect to the depth direction of the medium, which direction coincides with the direction along which the light beam is irradiated to the medium. The backward scattered light beam that undergoes the interference is limited to the light, which is radiated from the predetermined position in accordance with the optical path difference described above. This is because the light beam is the low coherence light beam having a short coherence length.

The intensity of the interference light beam having been obtained in the manner described above is detected. Optical heterodyne detection of the intensity of the backward scattered light beam is carried out in accordance with the detected intensity of the interference light beam. The intensity of the backward scattered light beam, which has thus been detected, carries the information representing the microstructure at the predetermined depth in the medium. Therefore, the tomographic information of the medium can be obtained in accordance with the intensity of the backward scattered light beam.

As described above, with the method and apparatus for obtaining tomographic information in accordance with the present invention, both the reference light beam and the signal light beam carrying the tomographic information of the medium pass through the same optical path. Therefore, even if external vibrations or thermal disturbance occurs on the two light beams, the external vibrations or the thermal disturbance will not have different effects on the two light beams. Therefore, the intensity of the signal light beam can be detected with a high S/N ratio, and the tomographic information of the medium can be obtained with a high S/N ratio.

Also, in cases where the length of the optical path of at least either one of the two split light beams is modulated, the tomographic information at an arbitrary depth in the medium can be obtained.

DESCRIPTION OF THE PREFERRED EMBODIMENTS

The present invention will hereinbelow be described in further detail with reference to the accompanying drawings.

Figure 1:
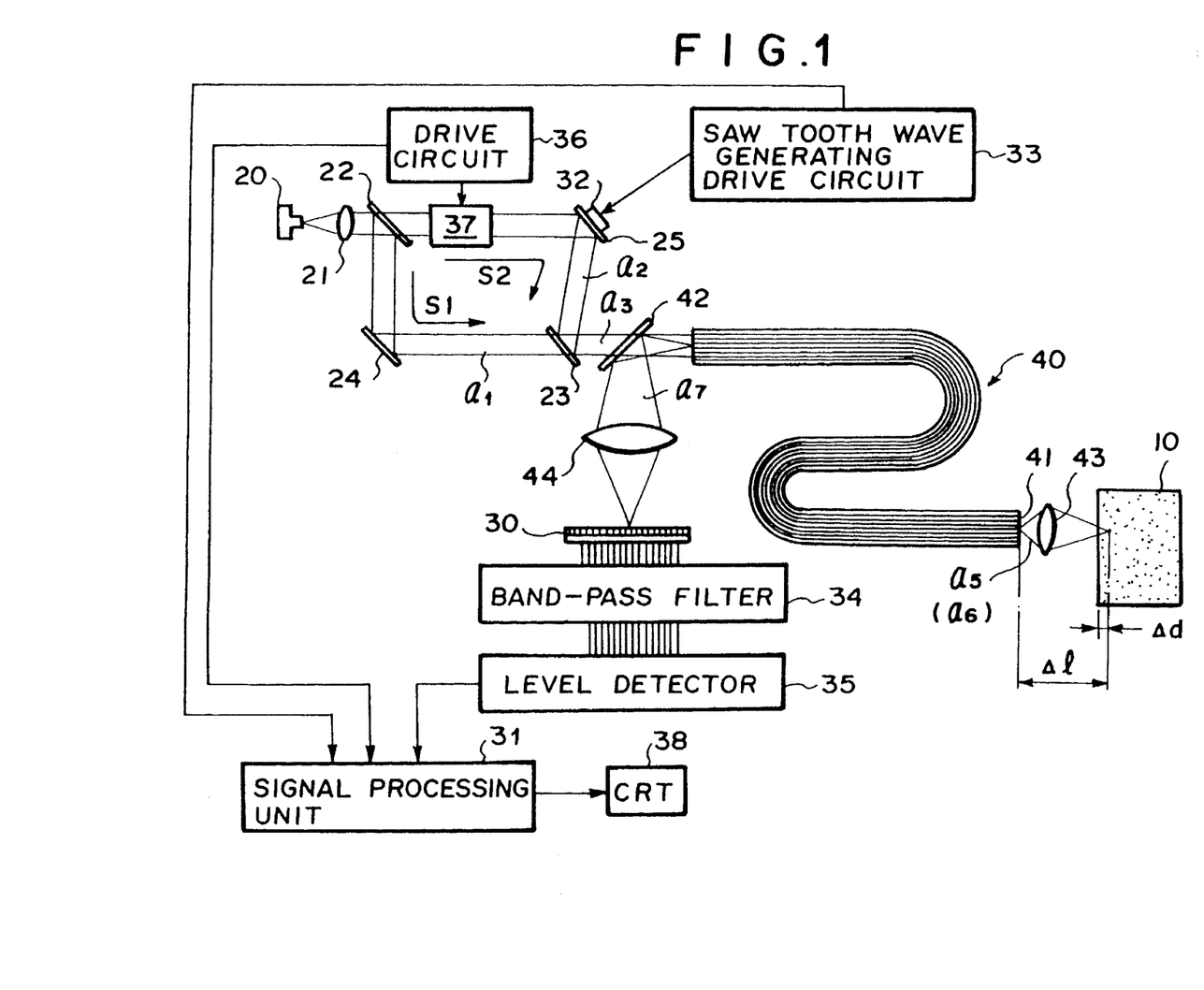
FIG. 1 is a block diagram showing an embodiment of the apparatus for obtaining tomographic information in accordance with the present invention.

FIG. 1 is a block diagram showing an embodiment of the apparatus for obtaining tomographic information in accordance with the present invention. The apparatus for obtaining tomographic information, which is shown in FIG. 1, comprises an SLD (super-luminescent diode) light source 20 for producing an SLD light beam having a frequency $\omega 0$, and a collimator lens 21 for collimating the light beam, which has been produced by the SLD light source 20. The apparatus for obtaining tomographic information also comprises beam splitters 22, 23 and mirrors 24, 25 for splitting the SLD light beam, which has been collimated by the collimator lens 21, into a first light beam a1 and a second light beam a2, causing the first light beam a1 and the second light beam a2 to travel respectively along a first optical path S1 having an optical path length L1 and a second optical path S2 having an optical path length L2 (wherein L2–Li>L0, where L0 represents the coherence length of the SLD light beam produced by the SLD light source 20), and thereafter superposing the first light beam a1 and the second light beam a2 one upon the other. The apparatus for obtaining tomographic information further comprises a piezoelectric device 32, which is located in the second optical path S2 and which sweeps the phase of the second light beam a2 in a saw tooth wave form and thereby shifts the frequency of the second light beam a2 to a frequency $\omega 1$ slightly different from the original frequency $\omega 0$, and a saw tooth wave generating drive circuit 33 for generating a signal, which drives the piezo-electric device 32. The apparatus for obtaining tomographic information still further comprises an optical path length modulating means 37 for modulating the optical path length L2 of the second optical path S2, and a drive circuit 36 for driving the optical path length modulating means 37. The apparatus for obtaining tomographic information also comprises a multimode image optical fiber bundle 40 for guiding a combined light beam a3, which has been obtained from the beam splitter 23, to a position in the vicinity of a medium 10, and a semi-transparent mirror 41, which is located on the end face of the image optical fiber bundle 40 on the side of the medium 10. The apparatus for obtaining tomographic information further comprises a condensing lens 43 for condensing a light beam a5, which is radiated out of the image optical fiber bundle 40. The apparatus for obtaining tomographic information still further comprises a beam splitter 42, which is located in the optical path of the combined light beam a3 impinging upon the image optical fiber bundle 40 and which changes the direction of travel of a light beam a7 returning from the image optical fiber bundle 40 (i.e. the light beam traveling reversely to the direction of incidence upon the image optical fiber bundle 40). The apparatus for obtaining tomographic information also comprises a condensing lens 44 for condensing the light beam a7, the direction of travel of which has been changed by the beam splitter 42, and a two-dimensional array photodetector 30 for detecting the light beam condensed by the condensing lens 44. The apparatus for obtaining tomographic information further comprises a band-pass filter 34, which allows a signal having a frequency of a predetermined band to pass therethrough, and a level detector 35 for detecting the level of the signal having passed through the band-pass filter 34. The apparatus for obtaining tomographic information still further comprises a signal processing unit 31 for calculating the intensity of a backward scattered light beam a6, which has been scattered from a predetermined depth in the medium, with the optical heterodyne detection technique in accordance with the signal level, which has been detected by the level detector 35, a signal, which is received from the saw tooth wave generating drive circuit 33 and represents the shifted frequency $\omega_1$ of the second light beam a2, and a signal, which is received from the drive circuit 36 and represents the optical path length L2 of the second optical path S2 after being modulated. The signal processing unit 31 thereafter obtains the information representing the microstructure with respect to the depth direction of the medium 10 in accordance with the calculated intensity of the backward scattered light beam a6.

The term "optical path length L1" as used herein means the optical path length taken along the first optical path S1 between the beam splitter 22 and the beam splitter 23. Also, the term "optical path length L2" as used herein means the optical path length taken along the second optical path S2 between the beam splitter 22 and the beam splitter 23. In general, the coherence length L0 takes a value falling within the range of approximately 40 μm to approximately 50 μm.

How this embodiment works will be described hereinbelow.

The SLD light beam, which has been produced by the SLD light source 20 and has the frequency $\omega_0$, is collimated by the collimator lens 21. The collimated light beam is split by the beam splitter 22 into the first light beam a1, which travels along the first optical path S1 having the optical path length L1, and the second light beam a2, which travels along the second optical path S2 having the optical path length L2. The frequency of the first light beam a1 is kept at the original frequency $\omega_0$, and the first light beam a1 having the frequency w0 impinges upon the beam splitter 23.

Figure 3:
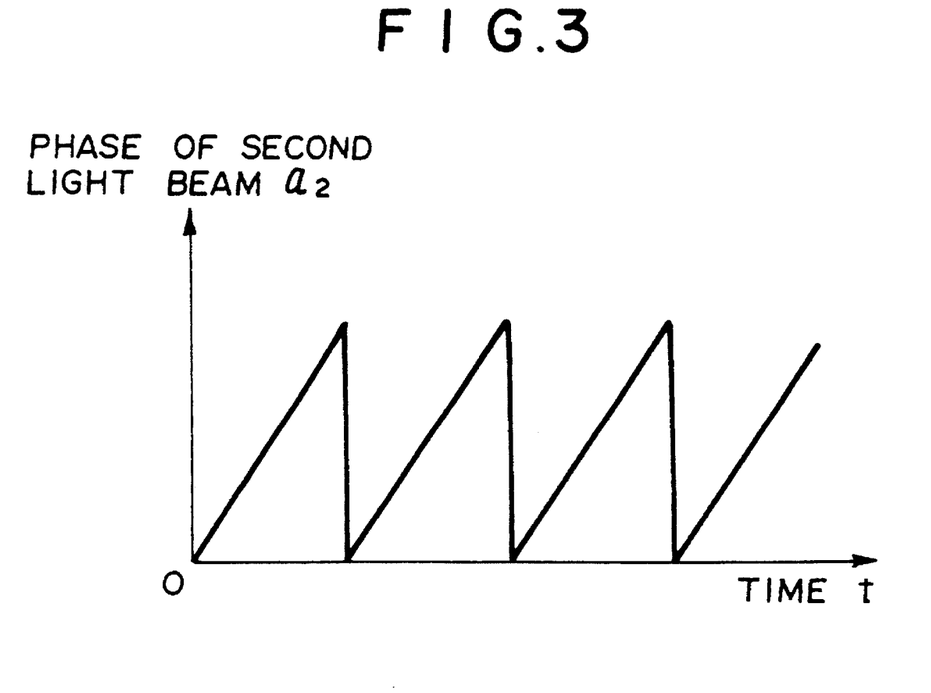
FIG. 3 is a graph showing how the phase of a second light beam a2 is swept in a saw tooth wave form by a piezo-electric device 32.

The optical path length L2 of the second optical path S2 is originally set by the optical path length modulating means 37 at a predetermined value, which satisfies the condition of (L2–L1)>L0. Also, as illustrated in FIG. 3, the phase of the second light beam a2 is swept in the saw tooth wave form by the mirror 25, which is driven by the piezo-electric device 32 in the saw tooth wave pattern. In this manner, the frequency of the second light beam a2 is shifted from the original frequency $\omega_0$ to the slightly different frequency $\omega_1$, and the second light beam a2 having the frequency $\omega_1$ impinges upon the beam splitter 23.

The two light beams a1 and a2 impinging upon the beam splitter 23 are combined with each other by the beam splitter 23, and the combined light beam a3 is thereby obtained. The combined light beam a3 passes through the beam splitter 42 and impinges upon the image optical fiber bundle 40. The optical path difference $\Delta L$ (=L2–L1) between the optical paths of the two light beams a1 and a2, which are combined with each other, is larger than the coherence length L0. Therefore, the combined light beam a3 is composed of the two light beams a1 and a2, which are merely superposed one upon the other without interfering with each other.

Figure 2:
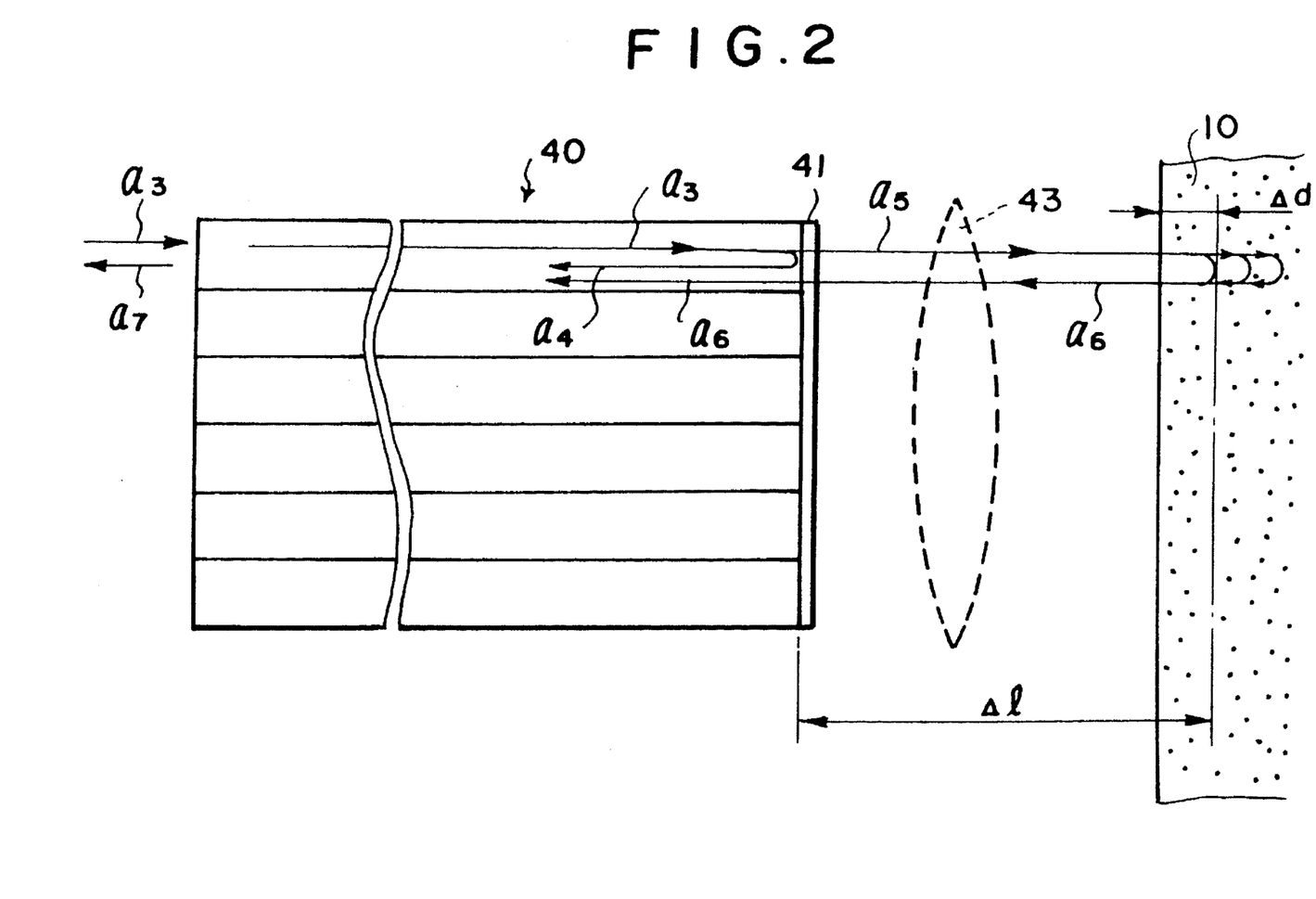
FIG. 2 is an explanatory view showing how a combined light beam a3 works after entering an image optical fiber bundle 40.

FIG. 2 is an explanatory view showing how the combined light beam a3 works after entering the image optical fiber bundle 40. As illustrated in FIG. 2, the combined light beam a3 impinging upon the image optical fiber bundle 40 is guided through the image optical fiber bundle 40 to the position in the vicinity of the medium 10, i.e. to the position spaced a distance of ($\Delta 1 - \Delta d$) from the surface of the medium 10. After the combined light beam a3 has been guided to the position in the vicinity of the medium 10, part of the combined light beam a3 (this part will hereinafter be referred to as the third light beam a4) is reflected by the semi-transparent mirror 41, which is located at the end of the image optical fiber bundle 40 on the side of the medium 10. The direction of travel of the third light beam a4 is thus reversed, and the third light beam a4 returns through the image optical fiber bundle 40. The remaining part of the combined light beam a3 (this part will hereinafter be referred to as the light beam a5) passes through the semi-transparent mirror 41 and emanates from the image optical fiber bundle 40. The light beam a5 is then condensed by the condensing lens 43 and is irradiated to medium 10.

The light beam a5, which has thus been irradiated to the medium 10, is reflected from the surface of the medium 10 or is scattered by the light scattering substance contained in the medium 10. Of the light beam having thus been reflected or scattered, the backward scattered light beam a6 passes through the condensing lens 43 and again impinges upon the image optical fiber bundle 40. The backward scattered light beam a6 contains not only the light, which has been scattered at a predetermined depth in the medium 10, but also the light, which has been scattered at various depths $\Delta d$ in the medium 10.

When the backward scattered light beam (i.e. the fourth light beam) a6, which contains the light scattered at various depths $\Delta d$ in the medium 10, impinges upon the image optical fiber bundle 40, it is combined with the third light beam a4, the direction of travel of which has been reversed by the semi-transparent mirror 41.

Each of the third light beam a4 and the fourth light beam a6 is composed of the component of the first light beam a1 (i.e., the light beam which has the frequency $\omega_0$ and has passed through the optical path having the optical path length L1) and the component of the second light beam a2 (i.e., the light beam which has the frequency $\omega_1$ and has passed through the optical path having the optical path length L2). Also, the optical path length of the fourth light beam a6 is longer by a value equal to two times the optical distance $\Delta 1$ than the optical path length of the third light beam a4. Therefore, when the third light beam a4 and the fourth light beam a6 are combined with each other, in cases where the optical distance ($2 \times \Delta 1$) is approximately equal to the difference $\Delta L$ between the optical path length L1 of the first light beam a1 and the optical path length L2 of the second light beam a2, the component of the second light beam a2, which is one of the components of the two light beams constituting the third light beam a4, and which has passed through the optical path having the longer optical path length than the optical path length of the other component, is caused to interfere with the component of the first light beam a1, which is one of the components of the two light beams constituting the fourth light beam a6, and which has passed through the optical path having the shorter optical path length than the optical path length of the other component. In this manner, the interference light beam a7 occurs. The optical intensity of the interference light beam a7 repeatedly becomes high and low at a frequency $\Delta\omega(=|\omega 0-\omega 1|)$ equal to the difference between the frequency $\omega 0$ of the first light beam a1 and the frequency $\omega 1$ of the second light beam a2.

The interference light beam a7, which has thus been generated by the interference in the region inside of the image optical fiber bundle 40, is radiated out of the other end of the image optical fiber bundle 40. The direction of travel of the interference light beam a7 is then changed by the beam splitter 42, and the interference light beam a7 impinges upon the condensing lens 44. The intensity of the interference light beam a7 is detected by the array of small photo detecting elements of the two-dimensional array photodetector 30. The detected optical intensity is photoelectrically converted, and only the signal representing the optical intensity repeatedly becoming high and low in the band including the aforesaid difference frequency $\Delta\omega$ is allowed to pass through the band-pass filter 34. The value of the signal is detected by the level detector 35.

The signal representing the intensity of the interference light beam a7 is fed from the level detector 35 into the signal processing unit 31 and is subjected to the optical heterodyne detection. In this manner, the intensity of the light beam, which is contained in the fourth light beam a6 and has been scattered from the predetermined depth in the medium 10, is calculated. As described above, the optical intensity, which has thus been calculated, represents the intensity of the light beam scattered from the predetermined depth in the medium 10, and therefore carries the information representing the microstructure located at the predetermined depth in the medium 10.

The operation described above is carried out with each of the fiber bundles, which constitute the image optical fiber bundle 40, and each of the photo detecting elements of the photodetector 30. In this manner, the information representing the two-dimensional microstructure located at the predetermined depth in the medium 10, i.e. the tomographic information at the predetermined depth, can be obtained. The optical path length modulating means 37 is driven by the drive circuit 36 in order to modulate the optical path length L2 of the second optical path S2, and the tomographic information at an arbitrary depth in accordance with the optical path difference $\Delta L$ can thereby be obtained.

The tomographic information at an arbitrary depth in the medium 10, which has thus been obtained, can be visualized by an image reproducing means, such as a cathode ray tube (CRT) display device 38 shown in FIG. 1.

As described above, with the apparatus for obtaining tomographic information in accordance with the present invention, both the reference light beam, which is employed for the optical heterodyne detection, and the signal light beam carrying the tomographic information of the medium pass through the same optical path. Therefore, even if external vibrations or thermal disturbance occurs on the two light beams, the external vibrations or the thermal disturbance will not have different effects on the two light beams. Therefore, the intensity of the signal light beam can be detected with a high S/N ratio, and the tomographic information of the medium can be obtained with a high S/N ratio.

The intensity of the backward scattered light beam a6 coming from the medium 10 is markedly lower than the intensity of the light beam incident upon the medium 10. Therefore, the transmittance of the semi-transparent mirror 41 should be adjusted appropriately such that the signal representing the intensity of the interference light beam may be optimized.

The optical path length L2 of the second optical path S2 need not necessarily be set to be longer than the optical path length L1 of the first optical path S1 and may be set such that (L1–L2)/L0. In such cases, if the optical distance $(2\times\Delta 1)$ is approximately equal to the difference $\Delta L'$ (=L1–L2) between the optical path length L1 of the first light beam a1 and the optical path length L2 of the second light beam a2, the component of the first light beam a1, which is one of the components of the two light beams constituting the third light beam a4, and which has passed through the optical path having the longer optical path length than the optical path length of the other component, will be caused to interfere with the component of the second light beam a2, which is one of the components of the two light beams constituting the fourth light beam a6, and which has passed through the optical path having the shorter optical path length than the optical path length of the other component. In this manner, the interference light beam a7 occurs.

What is claimed is:

1. A method for obtaining tomographic information, comprising the steps of:

i) splitting a low coherence light beam into a first light beam and a second light beam, which travel along first and second optical paths, respectively, ii) shifting an original frequency of said first light beam to a second frequency, which is slightly different from the original frequency of said first light beam, iii) combining said first light beam, having the second frequency, and said second light beam with each other at a position at which an optical path difference between said first optical path and said second optical path is larger than a coherence length of said low coherence light beam to produce a combined light beam, said first and second optical paths being different paths each beginning at a position at which said low coherence light beam is split into said first and second light beams and ending at a position at which said first and second light beams are combined, iv) guiding the combined light beam to a position in a vicinity of a medium, which has light scattering properties and tomographic information of which is to be obtained, v) splitting said combined light beam, which has been guided to the position in the vicinity of the medium, into a third light beam, which travels reversely to a direction of travel of said combined light beam, and a fourth light beam, which continues to travel along the direction of travel of said combined light beam and is thus irradiated to the medium, vi) combining a backward scattered light beam, which comes from the medium when said fourth light beam is irradiated onto the medium, and said third light beam with each other, vii) detecting an intensity of an interference light beam obtained from interference of:

a) a component of said first light beam and a component of said second light beam constituting said third light beam and which has passed through a longer of said first and second optical paths, and b) a second component of said first light beam and a second component of said second light beam constituting said backward scattered light beam and which has passed through a shorter of said first and second optical paths, viii) performing optical heterodyne detection of an intensity of said backward scattered light beam in accordance with the intensity of said interference light beam detected in said detecting step, to obtain information representing a microstructure of the medium at a predetermined depth in the medium, and ix) modulating an optical path length of one of the first and second optical paths arbitrarily to obtain information representing the microstructure at an arbitrary depth in the medium.

2. A method as defined in claim 1, further comprising the step of positioning the medium relative to a beam splitting position at which the combined light beam is split is step v) so that twice a distance between the beam splitting position and the predetermined depth within the medium is equal to approximately a difference between the lengths of said first and second optical paths.

3. A method as defined in claim 1, wherein said low coherence light beam is a light beam, which is produced by a super-luminescent diode.

4. An apparatus for obtaining tomographic information, comprising:

i) a light source for producing a low coherence light beam, ii) an optical system for splitting said low coherence light beam, which has been produced by said light source, into a first light beam and a second light beam, which travel along first and second optical paths, and combining said first light beam and said second light beam with each other at a position at which an optical path difference between said first optical path and said second optical path is larger than a coherence length of said low coherence light beam, to produce a combined light beam, said first and second optical paths being different paths each beginning at a position at which said low coherence light beam is split into said first and second light beams and ending at a position at which said first and second light beams are combined, iii) a frequency shifter for shifting an original frequency of said first light beam to a second frequency, which is slightly different from the original frequency of said first light beam, iv) light guide means for guiding the combined light beam to a position in a vicinity of a medium, which has light scattering properties and tomographic information of which is to be obtained, v) an optical member for splitting said combined light beam, which has been guided to the position in the vicinity of the medium, into a third light beam, which travels reversely to a direction of travel of said combined light beam, and a fourth light beam, which continues to travel along the direction of travel of said combined light beam and is thus irradiated onto the medium, said optical member thereafter combining a backward scattered light beam, which comes from the medium when said fourth light beam is irradiated onto the medium, and said third light beam with each other, vi) a photodetector for detecting an intensity of an interference light beam obtained from interference of:

a) one of a component of said first light beam and a component of said second light beam constituting said third light beam and which has passed through a longer of said first and second optical paths, and b) one of a second component of said first light beam and a second component of said second light beam constituting said backward scattered light beam and which has passed through a shorter of said first and second optical paths, vii) an optical heterodyne detection means for detecting an intensity of said backward scattered light beam in accordance with the intensity of said interference light beam, which has been detected by said photodetector, to obtain information representing a microstructure of the medium at a predetermined depth in the medium, and viii) an optical path length modulating means disposed in either one of the first and second optical paths for modulating a length of the one of the first and second optical paths in which said optical path length modulating means is disposed to obtain information representing the microstructure at an arbitrary depth in the medium.

5. An apparatus as defined in claim 4, wherein said light source is a super-luminescent diode.

6. An apparatus as defined in claim 4, wherein said optical member is a semi-transparent mirror, and said light guide means is an optical fiber bundle.

7. An apparatus as defined in claim 4, further comprising means for positioning the medium relative to a beam splitting position at which the combined light beam is split is by the optical member so that twice a distance between the beam splitting position and the predetermined depth within the medium is equal to approximately a difference between the lengths of said first and second optical paths.

* * * * *